US00PP36040P2

(12) United States Plant Patent
Lim

(10) Patent No.: US PP36,040 P2
(45) Date of Patent: Jul. 30, 2024

(54) CLIMBER ROSE PLANT NAMED 'LIMsummer'

(50) Latin Name: *Rosa hybrida*
Varietal Denomination: LIMsummer

(71) Applicant: Altman Specialty Plants Inc., Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/371,544

(22) Filed: Sep. 22, 2023

(51) Int. Cl.
*A01H 5/02* (2018.01)
*A01H 6/74* (2018.01)

(52) U.S. Cl.
USPC ..... Plt./109
CPC ..... *A01H 6/749* (2018.05)

(58) Field of Classification Search
USPC ..... Plt./109
CPC ..... A01H 6/749; A01H 5/02
See application file for complete search history.

*Primary Examiner* — Keith O. Robinson
(74) *Attorney, Agent, or Firm* — Cassandra Bright

(57) ABSTRACT

A new and distinct cultivar of climber rose plant named 'LIMsummer' is disclosed, characterized by late blooming, creamy-yellow and pink striped double flowers with a floral/cinnamon fragrance. Plants are vigorous climbers, and can be grown on their own roots. The new variety is normally produced as an outdoor garden or container plant.

1 Drawing Sheet

Latin name of the genus and species: *Rosa hybrida.*
Variety denomination: 'LIMsummer'.

BACKGROUND OF THE INVENTION

The new *Rosa* cultivar is a product of a planned breeding program conducted by the inventor, Peter Lim. The objective of the breeding program was to produce vigorous new garden rose varieties with continuous blooming for ornamental commercial applications. The cross resulting in this new variety was made during June of 2009 in McMinnville, Oregon.

The seed parent is the unpatented variety *Rosa* 'BAIoad', U.S. Plant Pat. No. 19,046. The pollen parent is the unpatented variety *Rosa* 'Fiesta'. The new variety was selected in July of 2010 by the inventor in a group of seedlings resulting from the 2009 crossing, in a nursery in McMinnville, Oregon.

Asexual reproduction of the new cultivar has been performed by vegetative cuttings. This was first performed at a research greenhouse in McMinnville, Oregon July of 2010 and has shown that the unique features of this cultivar are stable and reproduced true to type in more than 5 successive generations.

SUMMARY OF THE INVENTION

The cultivar 'LIMsummer' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LIMsummer'. These characteristics in combination distinguish 'LIMsummer' as a new and distinct *Rosa* cultivar:

1. Creamy yellow and pink striped flowers.
2. Late season blooming.
3. Glossy foliage resistant to black spot and powdery mildew disease.
4. Vigorous climbing plant.
5. Abundant flowering after the second year of planting.
6. Plants can be grown on their own roots; grafting is not required.

PARENT COMPARISONS

Plants of the new cultivar 'LIMsummer' are similar to plants of the seed parent, in most horticultural characteristics, however, plants of the new cultivar 'LIMsummer' differ in the following:

1. Flower color of the new variety is yellow and pink, while the flower color of the seed parent is yellow.

Plants of the new cultivar 'LIMsummer' are similar to plants of the pollen parent in most horticultural characteristics, however, plants of the new cultivar 'LIMsummer' differ in the following:

1. Flower color of the new variety is yellow and pink, while the flower color of the pollen parent is pink and white.

COMMERCIAL COMPARISONS

Plants of the new cultivar 'LIMsummer' can be compared to the commercial variety *Rosa* 'WEKbecfoj', U.S. Plant Pat. No. 18,033. These varieties are similar in most horticultural characteristics, however 'LIMsummer' differs in the following:

1. Flowers of the new variety have more petals than flowers of this comparator.
2. Flowers of the new variety are smaller than flowers of this comparator.

Plants of the new cultivar 'LIMsummer' can also be compared to the commercial variety *Rosa* 'Meiteratol', U.S.

Plant Pat. No. 22,470. These varieties are similar in most horticultural characteristics, however 'LIMsummer' differs in the following:

1. Flower color of the new variety is yellow and pink, while the flower color of this comparator is pink and white.
2. Flowers of the new variety have fewer petals than flowers of this comparator.

BRIEF DESCRIPTION OF THE PHOTOGRAPH

The accompanying photograph illustrates in full color a close up of an individual flower from a plant of about 18 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LIMsummer' plants grown outdoors, in Palm Desert, California. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.
Botanical classification: *Rosa* 'LIMsummer'.
Market classification: Climber rose.

PROPAGATION

Time to initiate roots: About 15 days at approximately 20° C.
Time to produce a rooted cutting: About 35 days at approximately 20° C.

PLANT

Age of plant described: Approximately 1.5 years.
Growth habit: Climber about 6 to 7 feet in height at maturity.
Container size: 2 gallon.
Height: 60 cm.
Plant spread: 40 cm.
Rootstock: Own root.
Growth rate: Vigorous.
Branching characteristics: Sympodial branching.
Length of primary lateral branches: Average range 25 to 38 cm.
Diameter of primary lateral branches: Approximately 10 mm.
Quantity of branches: 4 to 5 main branches, moderate lateral branches, 10 to 20 lateral branches per main branch.
Branches-young wood:
*Diameter.*—Approximately 6 mm.
*Texture.*—Glabrous, moderate thorns.
*Color.*—Near RHS Green 137D.
Branches-old wood:
*Diameter.*—Approximately 10 mm.
*Color.*—Near RHS Green 137D, striated Grey-Brown 199B.
*Texture.*—Glabrous with some striations on oldest wood.
*Thorns.*—Approximate density/quantity of thorns: Moderate to dense. About 3 per 1 linear cm of stem on average. Young growth: Approximately 4 mm in diameter at base and 6 mm long. Colored near RHS Greyed-Orange 165B and 165C. Moderately hooked. Mature growth: About 10 mm at base, 11 mm long. Colored near RHS Greyed-Orange 177B. Very slightly hooked.

FOLIAGE

Leaf:
*Arrangement.*—Alternate and compound.
*Quantity.*—Average 8 to 12 per main branch.
*Internode.*—Average 3.0 cm to 7.5 cm.
*Average length.*—Approximately 7 cm.
*Average width.*—Approximately 5 cm.
Rachis:
*Average length.*—Approximately 2.3 cm.
*Average diameter.*—Approximately 2 mm.
*Color.*—Upper surface: Near RHS Green 137B. Lower surface: Near RHS Green 138B.
*Texture.*—Upper Surface: Glabrous. Lower Surface: Glabrous with a single small sharp thorn at leaflet pair nodes. Thorn about 2 mm long, colored near RHS Green 143C.
Leaflet:
*Quantity.*—5.
*Average length.*—Approximately 2.5 to 3.5 cm.
*Average width.*—Approximately 2.0 cm to 2.5 cm.
*Shape of blade.*—Broad ovate.
*Apex.*—Acute.
*Base.*—Broadly rounded.
*Margin.*—Serrate.
*Appearance of top surface.*—Strong glossy.
*Appearance of bottom surface.*—Matte.
*Texture of top surface.*—Glabrous.
*Texture of bottom surface.*—Glabrous.
*Color.*—Young foliage upper side: Near RHS Yellow-Green 144A. Young foliage under side: Near RHS Green 138B. Mature foliage upper side: Near RHS Green 139A. Mature foliage under side: Near RHS Green 138A.
*Venation.*—Type: Reticulate. Venation color upper side: Near RHS Yellow-Green 144A. Venation color under side: Near RHS Yellow-Green 144B.
Petiole:
*Average length.*—Approximately 1.5 cm.
*Average diameter.*—Approximately 2 mm.
*Color.*—Upper surface: Near RHS Yellow-Green 144A. Lower surface: Near RHS Green 137C.
*Petiole wing.*—Typically 11 mm long and 5 mm wide. Apex apiculate. Upper surface colored near RHS Green 143C, lower surface colored near Green 138B.
*Texture.*—Glabrous.

FLOWER

Natural flowering season: Spring until Autumn.
Inflorescence type and habit: Singly occurring fully double rotate flowers. Raised center of flower.
Rate of flower opening: Approximately 5 days from bud to fully opened flower.
Flower Longevity on plant: About 1 week.

Quantity of flowers: 20 to 30 fully opened flowers and buds.

Flower shape:

*From above.*—Round to very slightly irregular round.

*Profile of upper part of flower.*—Conical.

*Profile of lower part of flower.*—Nearly flat, lowest petals 5 reflex down slightly.

Flower size:

*Diameter.*—Approximately 5 cm.

*Height.*—Approximately 2 cm.

Peduncle:

*Length.*—Average 1.5 cm.

*Diameter.*—3 mm.

*Color.*—Near RHS Green 138B.

*Texture.*—Glabrous.

Petals:

*Petal arrangement.*—Multiple rotate, overlapping whorls.

*Petal quantity.*—Average 25.

*Length.*—Average 2 cm.

*Width.*—Average 1.8 cm.

*Shape.*—Broad deltate.

*Margin.*—Entire, slightly ruffled.

*Apex.*—Rounded, irregularly notched.

*Base.*—Very broad attenuate.

*Texture.*—Glabrous all surfaces.

*Color.*—When opening: Upper surface: Near RHS Yellow 10D. Irregular streaks and blotches covering between 10 to 40% of petal surface colored near Red 53C. Basal blotch near Yellow 7C. Lower surface: Near RHS Yellow 10D. Irregular streaks and blotches covering between 10 to 40% of petal surface colored near Red 53D. Basal blotch near Yellow 7C. Fully opened: Upper surface: Near RHS Yellow 11D. Irregular streaks and blotches covering between 10 to 40% of petal surface colored near Red 53C and 53D. Basal blotch near Yellow 7D. Lower surface: Near RHS Yellow-Orange 19D. Irregular streaks and blotches covering between 10 to 40% of petal surface colored near Red 53C and 53D. Basal blotch near Yellow 7D. Aging: Upper surface: Near RHS Yellow-Orange 19D. Irregular streaks and blotches covering between 10 to 40% of petal surface colored near Red 55B, 55C and 55D. Basal blotch near Yellow 7D. Lower surface: Near RHS Yellow-Orange 19D. Irregular streaks and blotches covering between 10 to 40% of petal surface colored near Red 55B, 55C and 55D. Basal blotch near Yellow 7D.

Bud:

*Shape.*—Ovate.

*Length.*—Approximately 2.0 cm.

*Diameter.*—Approximately 1.3 cm.

*Color.*—Near RHS Yellow 4C flushed Red 55B and 55C.

Sepals:

*Quantity.*—5.

*Length.*—1.8 cm.

*Width.*—6 mm.

*Shape.*—Deltoid.

*Apex.*—Apiculate. Strong, frilled sepal extensions, flushed RHS Red 53C. Medium sepal extensions.

*Margin.*—Entire.

*Texture.*—Upper Surface: Pubescent. Lower surface: Glabrous.

*Color.*—Interior Surface: Near RHS Green 137B. Exterior Surface: Near RHS Green 137C.

Receptacle:

*Length.*—6 mm.

*Width.*—9 mm.

*Shape.*—Hemispherical.

*Color.*—Near RHS Yellow-Green 145C.

Fragrance: Moderate to strong floral/cinnamon scent.

REPRODUCTIVE ORGANS

Stamens:

*Quantity.*—About 50. Densely clustered in center, with about 10 loosely rotate around outer edge.

*Filament length.*—Approximately 4 mm to 5 mm.

*Filament color.*—Near RHS Yellow 10D.

Anthers:

*Length.*—1 mm to 2 mm.

*Shape.*—Narrow globular.

*Color.*—Near RHS Greyed-Orange 167A.

*Pollen.*—Color: Near RHS Greyed-Orange 167D. Quantity: Scant to moderate.

Pistil: Not observed.

OTHER CHARACTERISTICS

Seeds and fruits: Not observed.

Disease/pest resistance: Good overall resistance to normal pests of garden roses. Very good resistance to blackspot (*Diplocarpon rosae*) and powdery mildew (*Podosphaera pannosa*) diseases. In a three-year confidential field trial of garden roses the new variety 'LIMsummer' remains free of powdery mildew year-round while varieties planted nearby showed symptoms of powdery mildew.

What is claimed is:

1. A new and distinct cultivar of climber rose plant named 'LIMsummer' as herein illustrated and described.

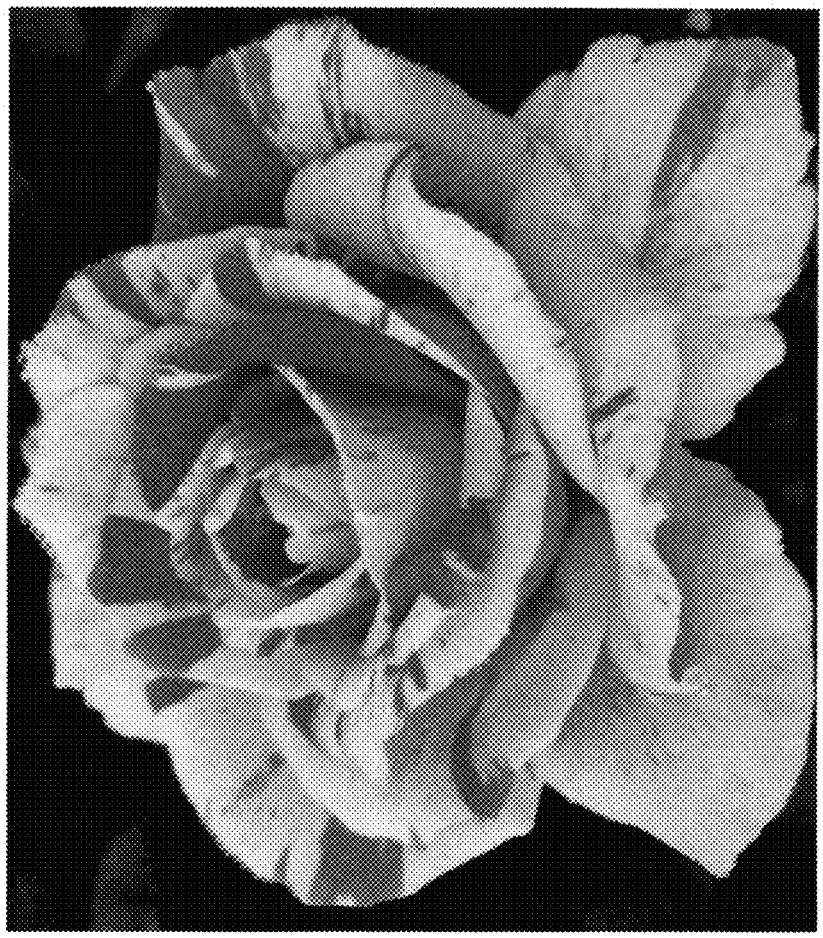

* * * * *